United States Patent
Palo, Jr.

(10) Patent No.: US 10,449,079 B2
(45) Date of Patent: *Oct. 22, 2019

(54) MULTI-FUNCTION BRACE

(71) Applicant: Matti Palo, Jr., Covington, LA (US)

(72) Inventor: Matti Palo, Jr., Covington, LA (US)

(*) Notice: Subject to any disclaimer, the term of this patent is extended or adjusted under 35 U.S.C. 154(b) by 462 days.

This patent is subject to a terminal disclaimer.

(21) Appl. No.: 15/056,561

(22) Filed: Feb. 29, 2016

(65) Prior Publication Data

US 2017/0246023 A1 Aug. 31, 2017

(51) Int. Cl.
*A61F 5/058* (2006.01)
*A61F 7/02* (2006.01)
*A61F 5/01* (2006.01)

(52) U.S. Cl.
CPC ........ *A61F 5/05866* (2013.01); *A61F 5/0118* (2013.01); *A61F 7/02* (2013.01); *A61F 2007/0225* (2013.01); *A61F 2007/0282* (2013.01)

(58) Field of Classification Search
CPC .... A61F 5/0118; A61F 5/05866; A61F 5/013; A61F 13/107; A61F 5/10; A61F 7/007; A61F 2013/00187; A61F 2007/0001; A61F 2013/00919; A61F 5/05875; A61F 2005/0186; A61F 2007/0035; A61F 2007/0036; A61F 13/104; A61F 2007/0037; A61F 2/586; A41D 13/08; A41D 13/088; A41D 13/065; A63B 71/143; A63B 71/14

See application file for complete search history.

(56) References Cited

U.S. PATENT DOCUMENTS

| | | | |
|---|---|---|---|
| 6,029,277 A * | 2/2000 | Picchione, II | A41D 19/01582 2/16 |
| 6,790,192 B2 * | 9/2004 | Robinson | A61F 5/0118 602/20 |
| 7,455,650 B1 * | 11/2008 | Garelick | A62B 23/06 128/878 |
| 8,246,560 B2 * | 8/2012 | Gaylord | A61F 5/0118 602/21 |
| 9,078,737 B2 | 6/2015 | Palo, Jr. | |
| 9,271,859 B2 * | 3/2016 | Palo, Jr. | A61F 5/0118 |
| 2013/0226057 A1 | 8/2013 | Palo, Jr. | |

* cited by examiner

*Primary Examiner* — Ophelia A Hawthorne
(74) *Attorney, Agent, or Firm* — The Rapacke Law Group, P.A.

(57) ABSTRACT

A brace may include a body portion and a finger portion. The body portion may include a first flexible sheet configured to receive at least portions of a user's wrist and hand and may restrict movement of the wrist. The finger portion may include a second flexible sheet and a rigid stabilizing member. The finger portion may be configured to receive at least one of the user's fingers and may restrict movement of the at least one finger relative to the wrist and hand. Further, the body portion be configured to releasably receive the finger portion.

20 Claims, 5 Drawing Sheets

MULTI-FUNCTION BRACE

FIELD

The present disclosure relates to a therapy brace and to a therapy kit comprising a therapy brace.

BACKGROUND

This section provides background information related to the present disclosure which is not necessarily prior art.

A human hand may include a median nerve that supplies muscle function and sensation to a thumb, an index finger, a middle finger (long finger), and half of a ring finger. Median neuropathy, known as carpal tunnel syndrome, leads to wasting of the thumb musculature (thenar eminence) and resultant weakness that may become permanent if left untreated. Furthermore, median neuropathy can cause numbness in the digits that may be permanent if untreated. A brace can be used as an alternative to or in addition to a surgical procedure to treat median neuropathy and/or other nerve, muscle, and/or joint conditions.

SUMMARY OF THE INVENTION

This section provides a general summary of the disclosure, and is not a comprehensive disclosure of its full scope or all of its features.

In one form, the present disclosure provides a convertible or multi-function brace that may include a body portion and a finger portion. The body portion may include a first flexible sheet configured to receive at least portions of a user's wrist and hand and that restricts movement of the wrist. The finger portion may include a second flexible sheet and a rigid stabilizing member. The finger portion may be configured to receive at least one of the user's fingers and may restrict movement of the at least one finger relative to the wrist and hand. Further, the body portion may be configured to releasably receive the finger portion. In use, the wearer wraps and secures the first flexible sheet around at least portions of a wrist and hand. At rest the wearer inserts the finger portion into the body portion to stabilize the fingers. During activity, the wearer may remove the finger portion to allow use of the fingers.

In another form, the present disclosure provides a therapy kit that may include a convertible or multi-function brace that performs the function of two conventional braces. The brace may include a body portion configured to be wrapped around a user's wrist and restrict movement of the wrist. As a first function, the brace may allow relative movement of the user's fingers relative to the wrist. The brace may receive a finger portion that may be attached to the body portion and may be configured to receive at least one of the user's fingers. As a second function, the brace may restrict movement of the at least one finger relative to the wrist.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

A more complete understanding of these embodiments, and the attendant advantages and features thereof, will be more readily understood by reference to the following detailed description when considered in conjunction with the accompanying drawings. The drawings described herein may not be to scale, are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
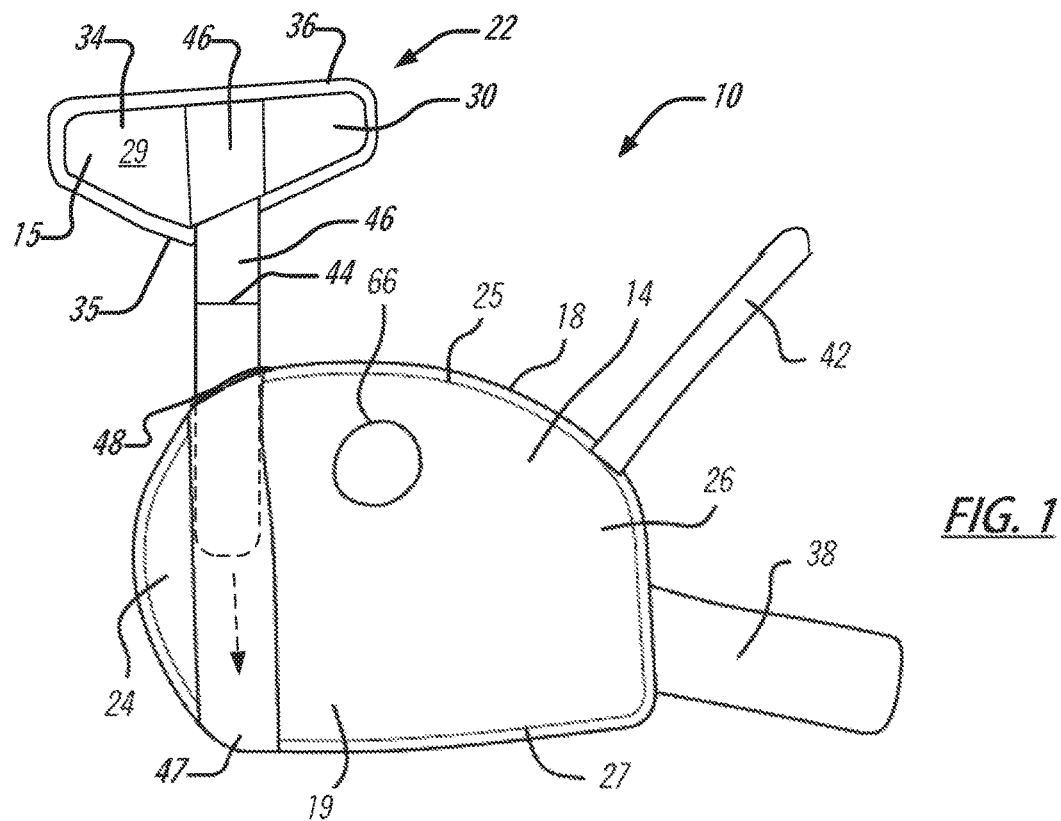
FIG. 1 is a plan view of a first side of a brace according to the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, methods, and kits to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers, and/or sections, these elements, components, regions, layers, and/or sections should not be limited by these terms. These terms may be only used to distinguish one element, component, region, layer, or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-10, the present disclosure provides a brace 10 configured to be secured to a user's wrist 11 and hand 12. The brace 10 may be used to treat injuries or conditions (for example only, carpel tunnel syndrome). The brace 10 may include a body portion 18 and a releasable finger portion 22. The body portion 18 and the finger portion 22 may be formed from first and second flexible sheets 14, 15, respectively. The first and second flexible sheets 14, 15 may be formed from a fabric material such as a foam material, for example, and may be capable of bi-directional elastic deformation. The fabric material is not limited to a foam material, but may be any material that provides the necessary functionality.

Figure 2:
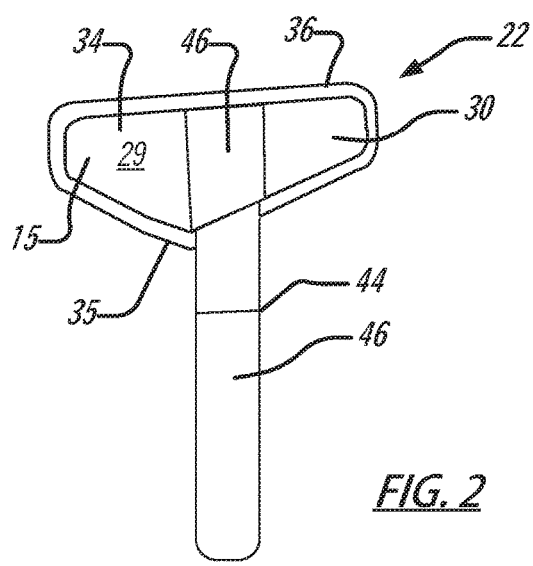
FIG. 2 is a plan view of a first side of the finger portion of the brace of FIG. 1.
Figure 3:
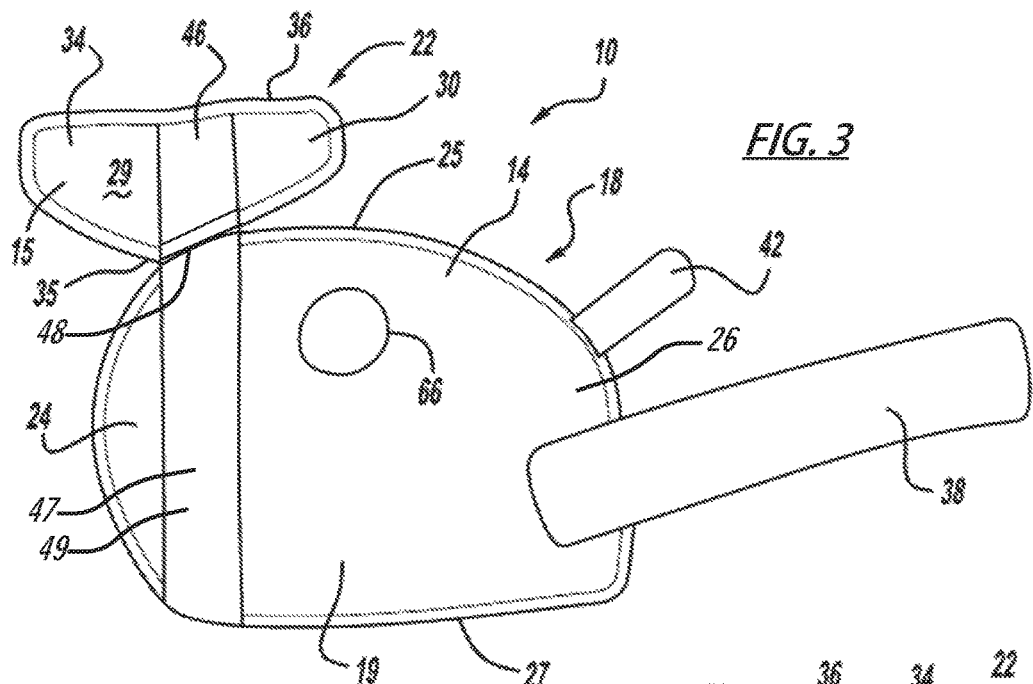
FIG. 3 is a plan view of a first side of a brace according to the principles of the present disclosure, with the finger portion fully received.
Figure 4:
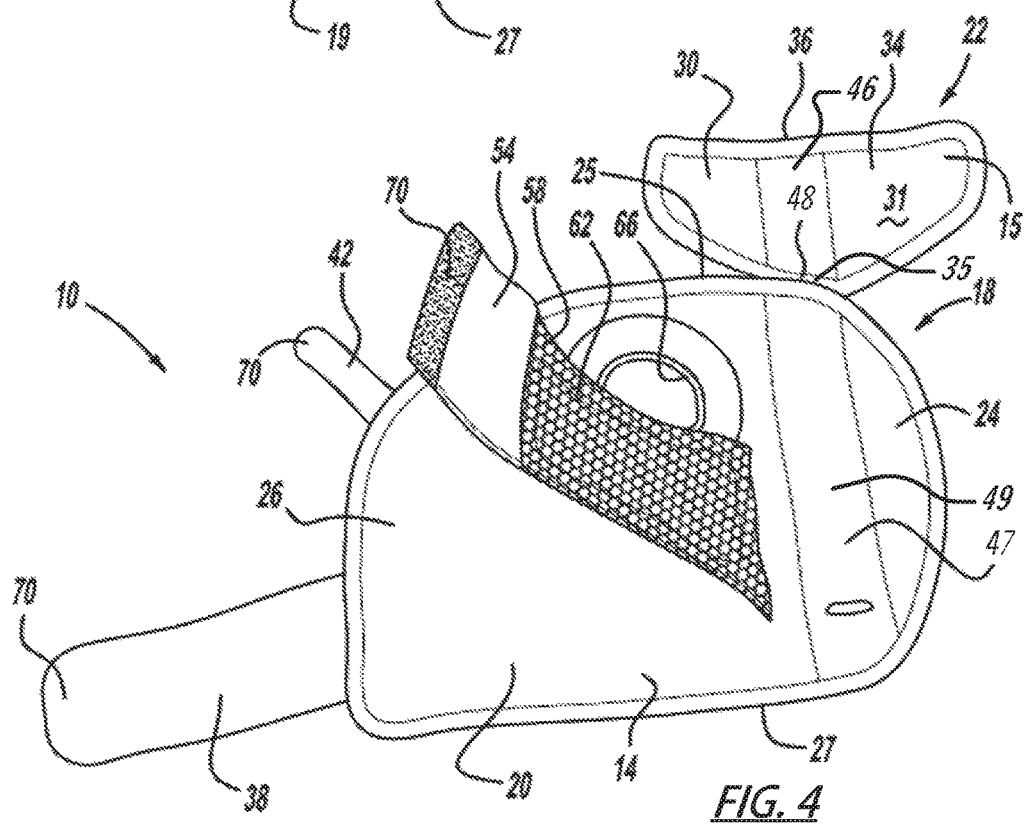
FIG. 4 is a plan view of a second side of the brace of FIG. 3.

As shown in FIGS. 1 and 2, the finger portion 22 may include a stabilizing member 46 that may be elongated and rigid, which may also be referred to as a spar or panel. The stabilizing member 46 may be inserted into a receiver 47 that, when worn, is oriented along the dorsal side of at least a portion of the wearer's wrist 11 and hand 12. The receiver 47 may be a sleeve or pocket 47 with an opening 48 to receive a stabilizing member 46 that provides support at least along the length of the finger portion 22. The spar 46 may be releasably or removably received to aid use by the wearer. Alternatively, the receiver 47 and the stabilizing member 46 may be configured to be otherwise releasably attached, such as by Velcro®, snaps, or other means. A first aid to the user is the ability to remove the finger portion 22 while wearing the body portion 18. A second aid to the user is the ability to remove the finger portion 22 with one hand, considering that the user is limited by an injured hand 12. A stabilizing member 46 may be comprised of metal, polymers, carbon, alloys, composites, or any other material that provides suitable stability. One of skill in the art will understand that a relatively thin and lightweight stabilizing member 46 may be desired for wearability. FIGS. 3 and 4 show the finger portion 22 of FIG. 1 fully inserted.

FIGS. 1 and 2 also illustrate a bend line 44 on the stabilizing member 46. In order for certain patients to avoid stiffness and pain, the stabilizing member 46 may be bent at 90 degrees at the point where the stabilizing member 46 exits the pocket 47. For example, patients with severe hand arthritis will benefit from a brace 10 that still holds the fingers 37, 39 partially extended (partially keeping the lumbricals out of the carpal tunnel) without as much stiffness as they will experience if their fingers are held straight all night. As another example, patients with metacarpal fractures in the second or third metacarpal may need to have their fingers 37, 39 bent at the knuckle joint (MCP joint) to 90 degrees to prevent stiffness the fracture heals. The stabilizing member 46 may be bent at a bend line 44 by the user, or the stabilizing member 46 may be pre-bent by the manufacturer. However, the stabilizing member 46 is not limited to bending, but may be formed as a 90° piece.

The body portion 18 may include a first side 19 (shown in FIGS. 1 and 3) and a second side 20 (shown in FIG. 4). The first and second sides 19, 20 may cooperate to form a first lateral end 24, a second lateral end 26, a first edge 25, and a second edge 27. An aperture 66 may be formed in the body portion 18 between the first and second lateral ends 24, 26 and may extend through the first and second sides 19, 20. In some embodiments, the aperture 66 may be disposed closer to the first edge 25 than the second edge 27.

Figure 6:
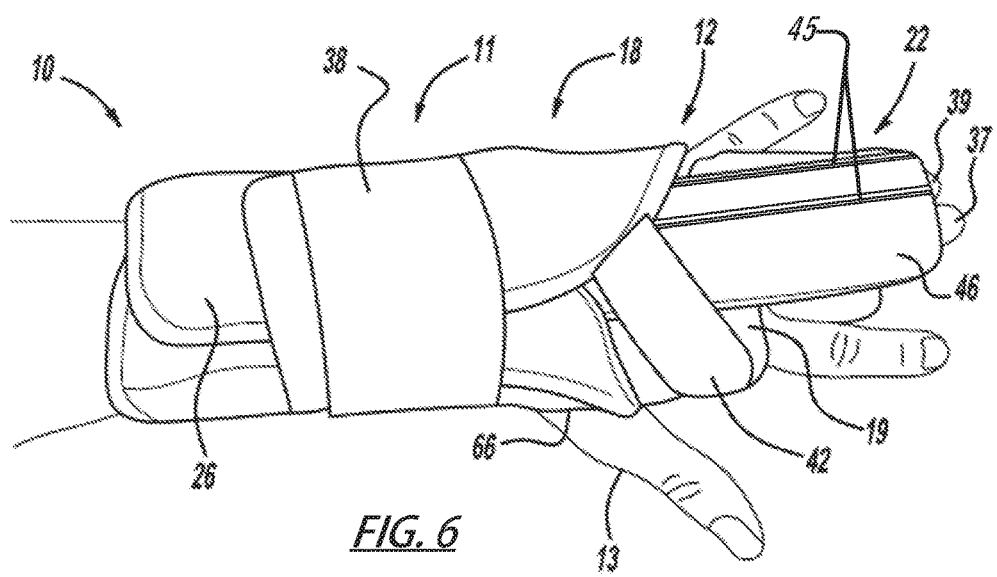
FIG. 6 is a perspective view of the brace further secured to the user's limb by an outer strap.
Figure 7:
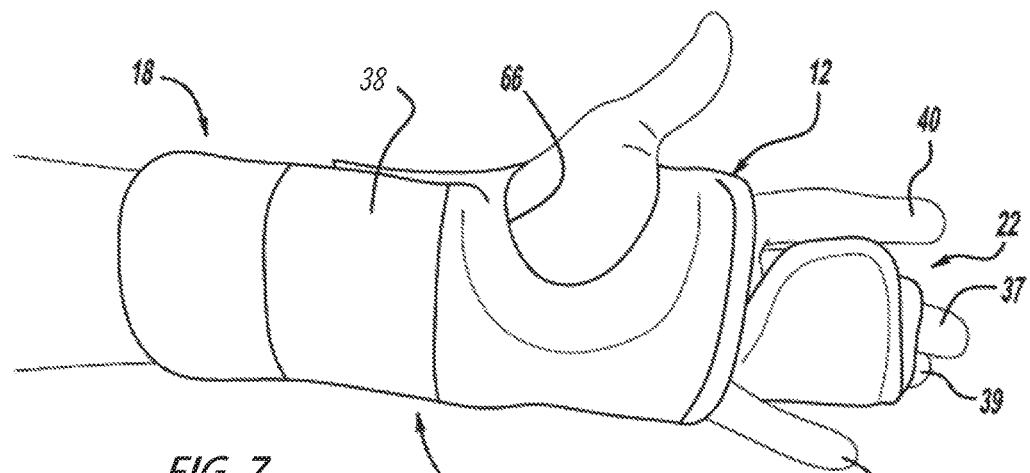
FIG. 7 is another perspective view of the brace secured to the user's limb.

The body portion 18 may also include a first outer strap 38, a second outer strap 42, and an inner strap 54. The first and second outer straps 38, 42 can be attached to the body portion 18 at or near the second lateral end 26. The first and second outer straps 38, 42 may be releasably secured to the first side 19 of the body portion 18 via a buckle (not shown) or via hook-and-loop retaining means (e.g., Velcro®) or any other suitable retaining means to secure the body portion 18 to the user's wrist 11 and hand 12, as shown in FIGS. 6 and 7.

Figure 5:
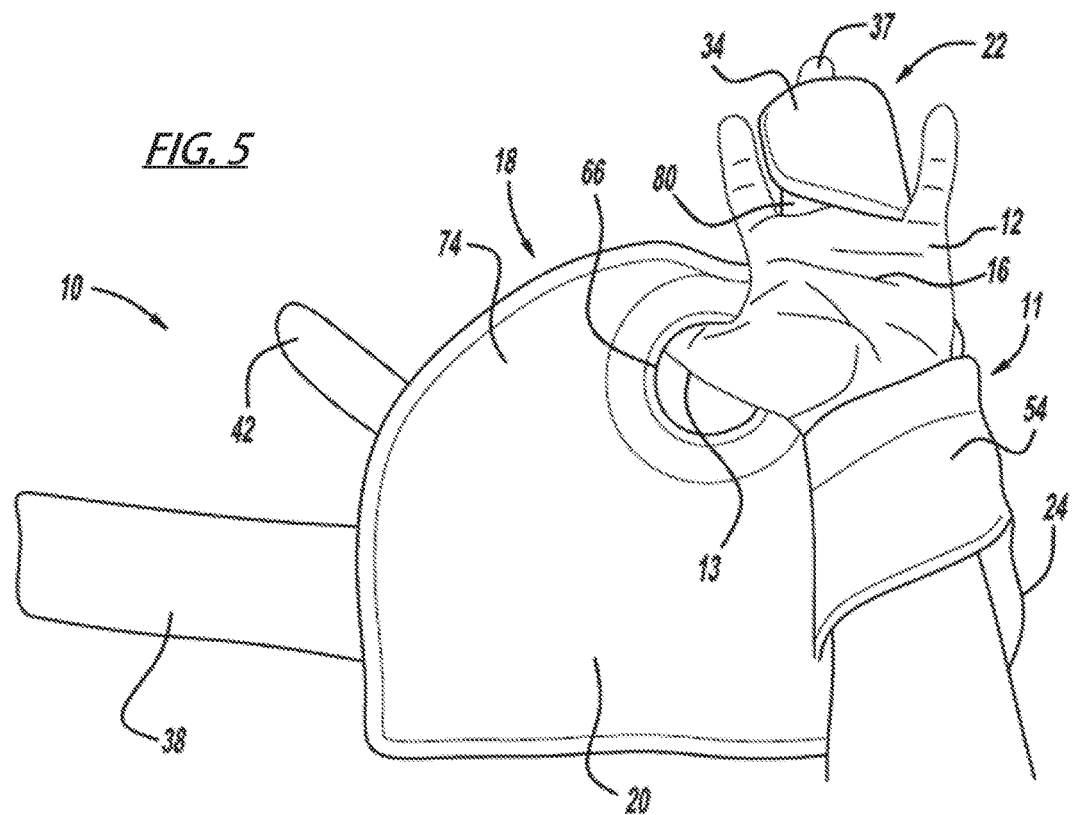
FIG. 5 is a perspective view of the brace secured to a user's limb by an inner strap.

The inner strap 54 may extend from the second side 20 of the body portion 18 between the first and second lateral ends 24, 26 as shown in FIG. 4 and may likewise by releasably secured, as shown in FIG. 5. The inner strap 54 may include a pocket 58 configured to removably receive an insert 62. The insert 62 may contain a gel or other material and may be heated or cooled for providing heating or cooling therapy for the user's wrist 11 and/or hand 12.

The finger portion 22 may include a first side 29 (shown in FIGS. 1-3) and a second side 31 (shown in FIG. 4). The first and second sides 29, 31 may cooperate to form first and second lateral ends 30, 34 and first and second edges 35, 36. The first and second lateral ends 30, 34 are unattached to and movable relative to the body portion 18. As will be subsequently described, the first and second lateral ends 30, 34 can be wrapped around one or more of a user's fingers 37, 39 and may be releasably secured to each other via a buckle (not shown) or hook-and-loop retaining means (e.g., Velcro®), for example, or any other suitable retaining means.

When worn, the detachable finger portion 22 may extend from the first edge 25 of the body portion 18. The stabilizing member 46 may extend at least partially between the second edge 27 of the body portion 18 and the second edge 36 of the finger portion 22. The stabilizing member 46 may be attached to the first side 29 or second side 31 of the finger portion 22. In some embodiments, the stabilizing member 46 can be received in a pocket 47 or pockets between the first sides 19, 29 and the second sides 20, 31.

With continued reference to FIGS. 1-10, operation of the brace 10 will be described in detail. The brace 10 may be worn by a user to treat injuries, degenerative conditions and/or other conditions such as carpal tunnel syndrome, for example. The brace 10 may be secured to the user's wrist 11, hand 12, and one or more fingers 37, 39 to support the wrist 11 and fingers 37, 39 and restrict movement of the wrist 11 and restrict movement of the fingers 37, 39 relative to a palm of the hand 12. Such support and restriction of motion may facilitate healing in the nerves, muscles, and/or other tissues in the wrist 11 and hand 12.

As shown in FIG. 5, the user may place his or her wrist 11 and hand 12 on the second side 20 of the body portion 18 and the user may place his or her middle and ring fingers 37, 39 (digitus tertius and digitus annularis), for example, on the second side 31 of the finger portion 22 such that dorsal sides of the wrist 11, hand 12 and the middle and ring fingers 37, 39 are in contact with the second sides 20, 31 and are generally aligned with the stabilizing member 46. The user may insert his or her thumb 13 through the aperture 66.

With the user's wrist 11, hand 12, and fingers 37, 39 in the position described above, the inner strap 54 may be wrapped around the wrist 11 and secured to the first side 19 of the first lateral end 24. In this manner, the insert 62 may be in heat transfer relation (for example, where the insert 62 provides either hot or cold therapy) with a palmar side of the wrist 11. As described above, the insert 62 may be heated or cooled prior to securing the brace 10 to the user's wrist 11.

Next, the brace 10 may be more firmly secured onto the wrist 11 and hand 12 by wrapping the first lateral end 24 around a circumference of the wrist 11 and at least a portion of the hand 12, as shown in FIGS. 6 and 7. The second lateral end 26 may or may not include a hook-and-loop retaining means (e.g., Velcro®) for attachment to the first lateral end 24. The first and second outer straps 38, 42 may be wrapped around the body portion 18 and the user's wrist 11 and/or hand 12 and may be removably attached to the first side 19 of the body portion 18. The first lateral end 30 and second lateral end 34 of the finger portion 22 may embrace or envelope the middle and ring fingers 37, 39 by wrapping the first and second lateral ends 30, 34 around the circumference of the fingers 37, 39. The first lateral end 30 may be removably attached to the second lateral end 34 on the palmar side of the fingers 37, 39 to secure the finger portion 22 to the middle and ring fingers 37, 39.

When the brace 10 is secured on the wrist 11, hand 12, and fingers 37, 39, the stabilizing member 46 or spar may be aligned with a posterior aspect of a radiocarpal joint overlying a dorsum of a carpus. The stabilizing member 46 may restrict movement of the wrist 11 and fingers 37, 39 and may align the wrist 11 and fingers 37, 39 in a neutral position, plus or minus two degrees. A neutral position may be defined as a position in which the wrist 11 and/or fingers 37, 39 are in approximately flat or planar positions (e.g., the wrist 11, the dorsal side of the hand 12, and/or the fingers 37, 39 are generally coplanar with or straight relative to the user's forearm). For example, the stabilizing member 46 may be approximately flat or planar, or the stabilizing member 46 may form an angle of approximately two degrees or less at the wrist 11. By supporting the middle and ring fingers 37, 39 in a straight, neutral position, metacarpophalangeal joints (knuckles) on the index and pinky fingers 40, 41 will also be aligned in a straightened position due to anatomical factors. If the middle and ring fingers 37, 39 are supported by the finger portion 22 in the neutral position, the index and pinky fingers 40, 41 will naturally rest in the neutral position also. Further, the brace 10 may cover knuckles on the hand 12 where the fingers 37, 39, 40, 41 meet the hand 12 (i.e., the base knuckles or first joints) and help to support the pinky and ring fingers 40, 41 in the neutral position. Therefore, the same result can be achieved by only restricting two fingers 37, 39 instead of four which may be more comfortable for the user. Greater comfort promotes better healing by encouraging the user to wear the brace more faithfully.

In one form, the finger portion 22 is configured to cooperate or coact with the body portion 18 and the user's fingers 37, 39 to keep the rigid stabilizing member 46 within a receiving pocket 47. The rigid stabilizing member 46 may be snugly fit or firmly wedged into the pocket yet maintain some freedom of movement, allowing for slight adjustment for finger length and for easy removal of the finger portion 22. The finger portion 22 is not limited to this freely sliding configuration, but may include a means of quick lock and quick release to help secure the finger portion 22. As shown in FIG. 6, an outer strap 42 may wrap around the hand 12 and releasably attach to the stabilizing member 46. The stabilizing member or panel 46 may be of uniform width along its length or, for example, may be narrow in a receiving pocket 47 and narrower or wider over the fingers 37, 39. Further the stabilizing member 46 may comprise one or more profiles 45 to add strength and rigidity. For example, a profile 45 may be a lip at the edge of the stabilizing member 46, although a profile 45 is not limited to the edge of the stabilizing member or to a 90° angle. Inclusion of one or more strengthening profiles 45 on the stabilizing member 46 may help maintain the fingers 37, 39 in proper position.

Figure 8:
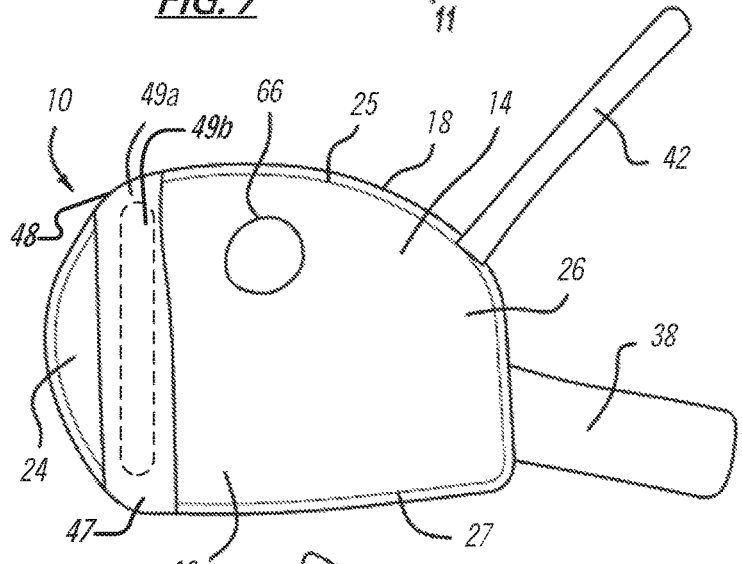
FIG. 8 is a plan view of a first side of a brace with the finger portion removed according to the principles of the present disclosure.
Figure 9:
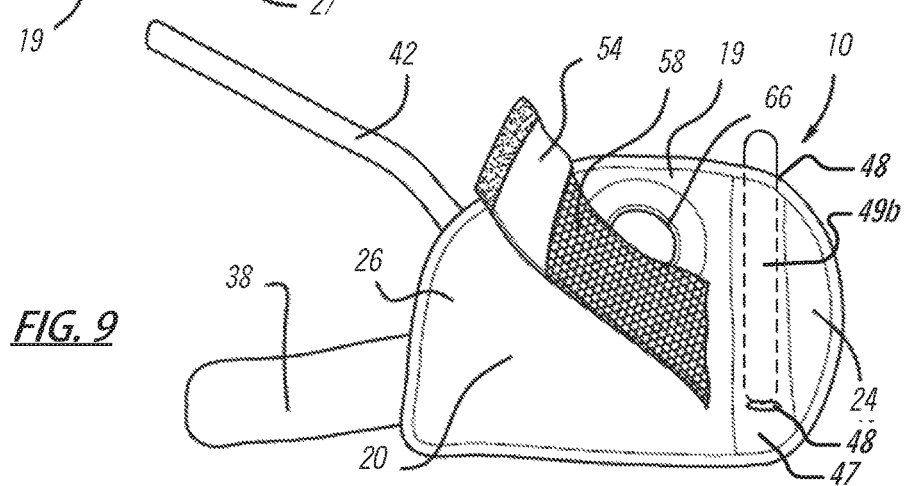
FIG. 9 is a plan view of a second side of the brace of FIG. 8.
Figure 10:
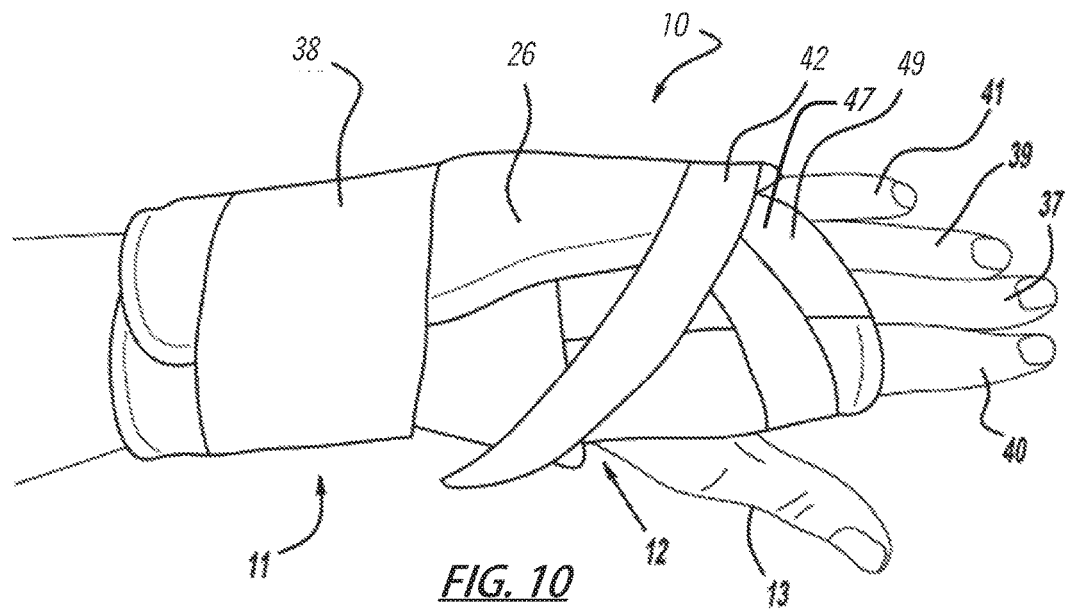
FIG. 10 is a perspective view of the brace, with the finger portion removed, secured to a user's limb according to the principles of the present disclosure.

As presented thus far, the brace 10 is a preferred embodiment for night use, while a wearer is resting or sleeping. A preferred embodiment for day use, when a wearer is more active and needs their fingers free, is shown in FIGS. 8-10. In practice, the user may move from rest to activity by removing the finger portion 22 of the brace 10 without unwrapping the brace 10, effectively transitioning from the configuration shown in FIGS. 6-7 to the configuration shown in FIG. 10. Similarly, the user may move from activity to rest by adding the finger portion 22 of the brace 10 without unwrapping the brace 10. The user does not need to unwrap the brace 10 to remove the stabilizing member 46. Thus, the brace 10 is more likely to remain on the user (day and night) and to fit the user's way of life, leading to increased protection and healing. In practice, the day and night configurations have similar efficacy. In at least these ways the present invention is an improvement over the prior art.

With reference to FIGS. 8-10, the parts of the brace 10 correspond to the parts of FIGS. 1-7. The inner strap 54 may or may not be angled in order to maximally cover the palmar surface of the hand and forearm. The inner strap may include a pocket 58 configured to removably receive the insert 62 (shown in FIG. 4), The insert may contain a gel or other material and may be heated or cooled for providing heating or cooling therapy for the user's wrist 11 and/or hand 12.

In some embodiments, as illustrated in FIGS. 8-10, the second outer strap 42 may be long enough to secure a bag of ice or any other cold or hot object to the first side 14 of the body portion 18. The second outer strap 42 may be angled (for example, at 45 degrees) across the wrist to apply heat or cold therapy to a distal side of the wrist.

The receiver 47 may comprise and/or receive at least a second stabilizing member 49. A stabilizing member 49a may be sewn or otherwise permanently attached to the body portion 18 to work in conjunction with any inserted stabilizing member 46 of a finger portion 22 and/or a stabilizing member 49b may be removably received in place of the stabilizing member 46 of a finger portion 22. A second stabilizing member 49 provides stability for the wrist 11 and hand 12 when the finger portion 22 is removed.

Operation of the brace 10 also corresponds from FIGS. 1-7 to FIGS. 8-10. When secured on the wrist 11 and hand 12, the body portion 18 of the brace 10 may allow unrestricted movement of the fingers 37, 39, 40, 41. The brace 10 may cover a portion of the hand 12 between the wrist 11 and a proximal palmar crease 16 (reference FIG. 7) on the palmar side of the user's hand to allow unrestricted movement of the fingers 37, 39, 40, 41. The knuckles on the user's hand 12 where the fingers 37, 39, 40, 41 meet the hand 12 (i.e., the base knuckles or first joints) may be exposed to allow unrestricted movement of the fingers 37, 39, 40, 41. The proximal palmar crease 16 may also be exposed to allow unrestricted movement of the fingers 37, 39, 40, 41.

Figure 11:
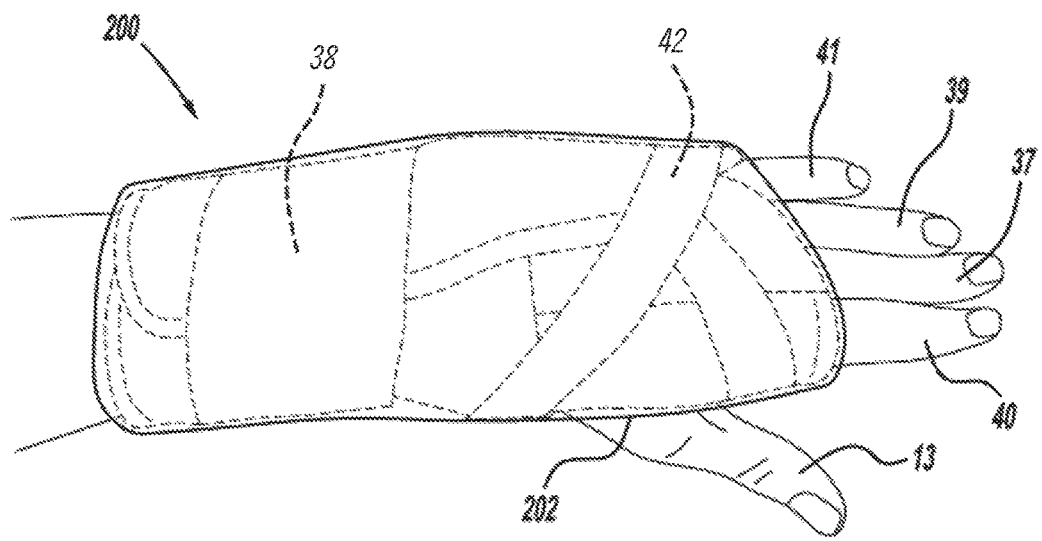
FIG. 11 is a perspective view of a sleeve covering the brace of FIG. 10.

With reference to FIG. 11, a sleeve 200 is provided that may be adapted to receive the hand 12 and wrist 11 and cover the brace 10. The sleeve 200 may include an aperture 202 to receive the user's thumb 13 and may be formed from a fabric such as a hi-directionally stretchable elastomer, for example. The sleeve 200 may be designed in various patterns or colors that the user may select from. The sleeve 200 may protect the first and second outer straps 38, 42 from being snagged on foreign objects. The sleeve 200 may also protect the user from being scratched by the brace 10. Further, the variety of colors and patterns of sleeves provides cosmetic advantages.

Referring now to FIGS. 1-11, the convertible and multi-function brace 10 may be packaged as a set or kit to treat injuries, degenerative conditions and/or other conditions such as carpal tunnel syndrome, for example. The packaged kit may include the body portion 18, the finger portion 22, at least a second stabilizing member 49, an additional stabilizing member 46 or entire finger portion pre-bent at 90 degrees along a bend line 44, cold/hot pack insert(s) 62, and a sleeve 200.

As discussed, the brace 10 without finger portion 22 can be worn during times when the user may be relatively active, such as when restricting movement of the middle and ring fingers 37, 39 is not practical. For example, the user may wear only the body portion 18 during the daytime or while the user is at work. The location of the stabilizing member 49 on the dorsum (top) of the hand 12 will improve functionality of the hand 12, and the brace 10 allows relatively unobstructed movement of all of the fingers 37, 39, 40, 41, which may allow the user to perform tasks such as driving or typing at a computer, for example.

The brace 10 with finger portion 22 can be worn during times of relative inactivity when restriction of movement of the middle and ring fingers 37, 39 can be tolerated by the user. For example, the user may wear the finger portion 22 at nighttime and/or while the user is sleeping or relaxing at home, for example.

Whether the brace 10 is sold by itself or in a kit, the brace 10 provides structure and functionality unrealized by the prior art. The convertible and multi-function design allows the consumer to purchase one brace 10 instead of two (day and night), which leads to savings and higher likelihood of proper treatment. The purchase decision is much easier. For the manufacturer and retailer, the multi-function design reduces the size and weight of the package for shipping and display space, and a reduced mice point increases unit sales. For the prescribing physician, the multi-function design ultimately results in healthier and happier patients. One of skill in the art will recognize that changes to structure may result in changes to cost, use, and healing.

While the brace 10 is described above as including one or more generally flat sheets 14, 15 having first and second ends that can be wrapped around the user's wrist 11 and/or fingers, in other embodiments the body portion 18 and/or finger portion 22 of the brace 10 may be formed as continuous, elastic sleeves that can be slid onto the user's wrist, hand, and/or fingers. In such embodiments, the brace 10 may be sized to accommodate specific users.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A brace comprising:
   a body portion including a first flexible sheet configured to receive at least portions of a user's wrist and hand, to restrict movement of the wrist, and to allow movement of all of the user's knuckles on all of the user's fingers relative to the wrist;
   a finger portion including:
      a rigid stabilizing member; and
      a second flexible sheet detachable from the body portion and configured to receive and wrap around only the user's middle two fingers and maintain the middle two fingers at a predetermined position relative to the wrist and hand;
   wherein the body portion is configured to releasably receive the finger portion and to locate the rigid stabilizing member along a dorsal side of a user's wrist and hand.

2. The brace of claim 1, wherein the rigid stabilizing member of the finger portion is configured to be inserted into a pocket or sleeve on the body portion.

3. The brace of claim 2, wherein the finger portion is configured to coact with the body portion and the user's fingers to maintain the rigid stabilizing member in the pocket or sleeve.

4. The brace of claim 1, wherein the finger portion is configured to wrap around a user's digitus tertius and digitus annularis.

5. The brace of claim 1, wherein the body portion is configured to maintain efficacy as a brace separate from the finger portion.

6. The brace of claim 1, further comprising at least one strap configured to be wrapped at least partially around the user's wrist or hand to secure the body portion thereon.

7. The brace of claim 1, wherein the finger portion is configured to be releasably attached to the body portion.

8. The brace of claim 1, wherein the body portion is configured to be wearable while the finger portion is being received or removed.

9. The brace of claim 1, further comprising at least a second rigid stabilizing member configured to replace the at least one rigid stabilizing member when the finger portion is removed from the body portion, or to be used in conjunction with the at least one rigid stabilizing member.

10. The brace of claim 1, the body portion further comprising a pocket configured to receive an insert for heating or cooling the wrist.

11. A therapy kit comprising:
- a body portion of a brace configured to receive at least portions of a user's wrist and hand, to restrict movement of the wrist, and to allow movement of all of the user's knuckles on all of the user's fingers relative to the wrist; and
- a finger portion of a brace including a rigid stabilizing member, the finger portion having a first flexible sheet detachable from the body portion and configured to receive and wrap around only the user's middle two fingers and maintain the middle two fingers at a predetermined position relative to the wrist and hand;
- wherein the body portion is configured to releasably receive the finger portion and to locate the rigid stabilizing member along a dorsal side of a user's wrist and hand; and
- wherein the body portion is configured to be worn by the user independently of the finger portion.

12. The therapy kit of claim 11, further comprising a cylindrical sleeve adapted to cover at least a portion of the body portion and/or finger portion.

13. The therapy kit of claim 11, further comprising at least a second rigid stabilizing member configured to replace the at least one rigid stabilizing member when the finger portion is removed from the body portion, or to be used in conjunction with the at least one rigid stabilizing member.

14. The therapy kit of claim 11, further comprising a rigid stabilizing member that is bent at 90 degrees.

15. The therapy kit of claim 11, further comprising hot and/or cold inserts.

16. The brace of claim 11, further comprising a strap configured to be positioned during use to be in-line with one or more nerves associated with carpal tunnel syndrome to maximize thermal transfer.

17. A brace comprising:
- a body portion including:
    - a first flexible sheet configured to receive at least portions of a user's wrist and hand, to restrict movement of the wrist, and to allow movement of all of the user's knuckles on all of the user's fingers relative to the wrist; and
    - at least one strap configured to be wrapped at least partially around the user's wrist or hand to secure the body portion thereon;
- a finger portion including:
    - a rigid stabilizing member; and
    - a second flexible sheet detachable from the body portion and configured to wrap around only a user's digitus tertius and digitus annularis and to maintain the user's digitus tertius and digitus annularis at a predetermined neutral position relative to the wrist and hand;
- wherein the body portion is configured to releasably receive the finger portion and to locate the rigid stabilizing member along a dorsal side of a user's wrist and hand.

18. The brace of claim 17, wherein the rigid stabilizing member of the finger portion is configured to be inserted into a pocket or sleeve on the body portion; and wherein the body portion is configured to be wearable while the finger portion is being received or removed.

19. The brace of claim 18, wherein the finger portion is configured to coact with the body portion and the user's fingers to maintain the rigid stabilizing member in the pocket or sleeve.

20. The brace of claim 17, further comprising at least a second rigid stabilizing member configured to replace the at least one rigid stabilizing member when the finger portion is removed from the body portion, or to be used in conjunction with the at least one rigid stabilizing member.

\* \* \* \* \*